(12) United States Patent
Borovik et al.

(10) Patent No.: US 7,439,318 B2
(45) Date of Patent: *Oct. 21, 2008

(54) METHOD FOR TRACE WATER ANALYSIS IN CYCLIC SILOXANES USEFUL AS PRECURSORS FOR LOW DIELECTRIC CONSTANT THIN FILMS

(75) Inventors: Alexander S. Borovik, Elmsford, NY (US); Ziyun Wang, Bethel, CT (US); Chongying Xu, New Milford, CT (US); Thomas H. Baum, New Fairfield, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/685,659

(22) Filed: Mar. 13, 2007

(65) Prior Publication Data

US 2007/0155931 A1 Jul. 5, 2007

Related U.S. Application Data

(63) Continuation of application No. 10/107,885, filed on Mar. 27, 2002, now Pat. No. 7,189,571.

(51) Int. Cl.
*G01N 25/56* (2006.01)
*C08F 6/06* (2006.01)

(52) U.S. Cl. .................. 528/483; 528/491; 528/493; 436/39; 436/72

(58) Field of Classification Search .............. None
See application file for complete search history.

(56) References Cited

U.S. PATENT DOCUMENTS

| | | | | |
|---|---|---|---|---|
| 4,122,247 | A | * | 10/1978 | Evans .................. 528/14 |
| 4,257,775 | A | | 3/1981 | Ladov et al. |
| 6,368,359 | B1 | | 4/2002 | Perry et al. |
| 6,383,955 | B1 | | 5/2002 | Matsuki et al. |
| 6,410,463 | B1 | | 6/2002 | Matsuki |
| 7,108,771 | B2 | | 9/2006 | Xu et al. |
| 7,189,571 | B1 | | 3/2007 | Borovik et al. |
| 2003/0116421 | A1 | * | 6/2003 | Xu et al. .................. 203/41 |

OTHER PUBLICATIONS

Hanson, K.J., et al., "Determination of trace water in propylene carbonate using hexafluoroacetone", "J. Electroanal. Chem.", Sep. 25, 1987, pp. 107-117, vol. 234, No. 1-2.

Mantz, R.A., et al., "Thermolysis of Polyhedral Oligomeric Silsesquioxane (POSS) Macromers and POSS-Siloxane Copolymers", "Chem. Mat.", Jun. 1996, pp. 1250-1259, vol. 8, No. 6.

* cited by examiner

*Primary Examiner*—Marc S Zimmer
(74) *Attorney, Agent, or Firm*—Steven J. Hultquist; Intellectual Property/Technology Law; Maggie Chappuis (57) ABSTRACT

An analytical technique for the accurate and precise measurement of trace water in chemical reagents, comprising the steps of combining a chemical reagent comprising ≦5 ppm water, with hexafluoroacetone (HFA), to form a sample mixture comprising at least the chemical reagent and a water derivative of hexafluoroacetone; and measuring the concentration of the water derivative of hexafluoroacetone by gas chromatography.

20 Claims, 4 Drawing Sheets

METHOD FOR TRACE WATER ANALYSIS IN CYCLIC SILOXANES USEFUL AS PRECURSORS FOR LOW DIELECTRIC CONSTANT THIN FILMS

CROSS-REFERENCE TO RELATED APPLICATION

This is a continuation of U.S. patent application Ser. No. 10/107,885 filed Mar. 27, 2002, now U.S. Pat. No. 7,189,571 in the names of Alexander S. Borovik, Ziyun Wang, Chongying Xu and Thomas H. Baum for "METHOD FOR TRACE WATER ANALYSIS IN CYCLIC SILOXANES USEFUL AS PRECURSORS FOR LOW DIELECTRIC CONSTANT THIN FILMS," issued Mar. 13, 2007 as U.S. Pat. No. 7,189,571. The disclosure of said U.S. patent application Ser. No. 10/107,885 is hereby incorporated herein by reference, in its entirety. Priority is claimed under the provisions of 35 USC 120.

TECHNICAL FIELD OF THE INVENTION

The present invention relates generally to a method for measuring the water content in siloxanes, particularly, cyclic siloxanes, such as tetramethylcyclotetrasiloxane (TMCTS) useful as precursors to low dielectric constant thin films.

BACKGROUND OF THE INVENTION

As the need for integrated circuits for semiconductor devices having higher performance and greater functionality increases, device feature geometries continue to decrease. As device geometries become smaller, the dielectric constant of an insulating material used between conducting paths becomes an increasingly important factor in device performance.

As device dimensions shrink to less than 0.25 μm, propagation delay, cross-talk noise and power dissipation due to resistance-capacitance (RC) coupling become significant due to increased wiring capacitance, especially interline capacitance between the metal lines on the same level. These factors all depend critically on the dielectric constant of the separating insulator or inter-layer dielectric (ILD).

The use of low dielectric constant (k) materials advantageously lowers power consumption, reduces cross talk, and shortens signal delay for closely spaced conductors through the reduction of both nodal and interconnect line capacitances. Dielectric materials that exhibit low dielectric constants are critical in the development path toward faster and more power efficient microelectronics.

Alkyl silanes, alkoxy silanes and polyhedral oligomeric silsesquioxanes (POSS) and other materials comprised mainly of Si, C, O and H (SiCOH) are being evaluated aggressively for obtaining low dielectric constant (k) thin-films as interlayer dielectrics in an integrated circuit by a PECVD approach. The resulting films formed when using these precursors give dense SiCOH containing films, having dielectric constants in the range of from about 2.4 to 3.2.

Introducing porosity to the low-dielectric constant SiCOH films may serve to further lower the dielectric constant to values below 2.5.

One particular class of precursors, cyclosiloxanes, (i.e. 2,4,6,8-tetramethylcyclotetrasiloxane (TMCTS)) is being considered as a source material for the deposition of low dielectric constant (k) thin-films used as interlayer dielectrics in an integrated circuit. Cyclosiloxanes provide a thin film having an open crystal structures or cage structure (e.g. Mantz et al., "Thermolysis of Polyhedral Oligomeric Silsesquioxane (POSS) Macromers and POSS-Siloxane Copolymers", Chem. Mater., 1996, 8, 1250-1259). PECVD of thin films from such precursors results in open areas in the structure, which leads to low packing density and hence low k values.

Chemical vapor deposition (CVD) is the thin film deposition method of choice for large-scale fabrication of microelectronic device structures, and the semiconductor manufacturing industry has extensive expertise in its use.

The purification and reproducible delivery of cyclosiloxanes for CVD is extremely critical for full-scale commercialization of the thin-film process. At present the PECVD deposition process is suffering from irreproducible delivery due to polymerization of TMCTS within the delivery lines and process hardware. Questions related to the purification of TMCTS and elimination of the polymerization must be considered. The exact polymerization mechanism is presently not known. However, studies by the inventors of the instant invention indicate that catalytic polymerization of siloxanes occurs in the presence of water/moisture, acids and bases. Accordingly, there is a need in the art to reduce water content as well as other catalytic species from siloxanes, providing improved purity, stability and utility.

U.S. patent application Ser. No. 10/015,326, filed on Dec. 31, 2001 discloses a novel method for reducing water levels in cyclic siloxanes to levels as low as 2 ppm, by drying the material through physical absorption methods and/or azeotropic distillation. However, despite such efforts, a reliable method for the trace water analysis of cyclic siloxanes is not known.

Karl Fischer titration, a commonly used, quality control method for water analysis, fails to deliver accurate measurements of water for cyclosiloxane materials, as the Karl Fischer reagents are not compatible with many cyclosiloxanes. For example, Karl Fischer reagents based on the following redox reaction:

$$SO_2 + I_2 + 2H_2O \rightarrow H_2SO_4 + 2HI \qquad (1)$$

However, in the case of cyclosiloxanes, the $I_2$ reacts with the Si—H groups to give a false positive, according to the following mechanism (shown with tetramethylcyclotetrasiloxane):

and many cyclosiloxanes polymerize in the Karl Fischer reagents.

Fourier Transform Infra Red (FTIR) Spectroscopy, another commonly used analytical technique for measuring water concentrations in many chemicals has detection limits of greater than 40 ppm. As the acceptable water concentration for cyclic siloxanes may be on the order of less than 10 ppm, FTIR could not support such a measurement.

Gas Chromatography (GC) another commonly used analytical technique, reliably and accurately detects concentrations of volatile organics to levels of less than 5 ppm, by a vapor phase/substrate separation process in a capillary column. However, GC columns available for measurement of trace water fail to meet the same detection standards as for organic molecules, rendering the technique unacceptable for trace water measurements in cyclosiloxanes.

Accordingly, there is a need for an analytical method, which allows for the determination of trace water in cyclosiloxane materials.

Therefore, it is one objective of the present invention to develop an analytical technique for the measurement of trace water in cyclosiloxane materials.

It is a further objective of the present invention to develop an analytical technique for the accurate and precise measurement of trace water in cyclosiloxane materials having detection limits as low as 1 ppm.

It is a further objective of the present invention, to develop a method for the production of super dry cyclosiloxanes, which includes a means by which to efficiently and accurately measure the water content of the super dry cyclic siloxane material.

SUMMARY OF THE INVENTION

The present invention relates to the accurate and precise measurement of water concentration in chemical materials requiring trace water analysis. More specifically, the present invention relates to the measurement of trace water concentration in siloxane and cyclosiloxane compounds by measuring an organic derivative of water by gas chromatography.

The ensuing discussion relating primarily to cyclosiloxanes should therefore be understood to encompass all such materials, (solids, liquids and gases) where trace water analysis is required and/or necessary, including but not limited to chemicals for semiconductor manufacturing, ion implantation, manufacture of flat panel displays, medical treatment, water treatment, emergency breathing equipment, welding operations, space-based applications involving delivery of liquids and gases, pharmaceutical industry, lubricating oil industry, foodstuff industry, etc.

In one aspect, the present invention relates to a process for the measurement of trace water concentration in chemical reagents comprising same, such process comprising the steps of:
(1) combining a chemical reagent comprising trace water, with hexafluoroacetone (HFA), to form a sample mixture comprising at least the chemical reagent and a water derivative of hexafluoroacetone; and
(2) measuring the concentration of the water derivative of hexafluoroacetone by gas chromatography.

In a further aspect, the present invention relates to a process for the measurement of trace water concentration in cyclosiloxane compounds comprising:
(1) combining a cyclosiloxane compound comprising trace water, with hexafluoroacetone (HFA), to form a sample mixture comprising at least the cyclosiloxane compound and a water derivative of hexafluoroacetone; and
(2) measuring the concentration of the water derivative of hexafluoroacetone by gas chromatography.

In a still further aspect, the present invention relates to a process for the measurement of trace water concentration in tetramethylcyclotetrasiloxane (TMCTS), wherein said process comprises the steps of:
(1) combining tetramethylcyclotetrasiloxane comprising trace water, with hexafluoroacetone (HFA) to form a sample mixture comprising at least tetramethylcyclotetrasiloxane and a water derivative of hexafluoroacetone; and
(2) measuring the concentration of the water derivative of hexafluoroacetone by gas chromatography.

In a further aspect, the present invention relates to an analytical technique for the accurate and precise measurement of trace water in chemical reagents comprising:
(1) combining a chemical reagent comprising $\leq 5$ ppm water, with hexafluoroacetone (HFA), to form a sample mixture comprising at least the chemical reagent and a water derivative of hexafluoroacetone; and
(2) measuring the concentration of the water derivative of hexafluoroacetone by gas chromatography.

In a further aspect, the present invention relates to an analytical technique for the accurate and precise measurement of trace water in cyclic siloxane materials comprising:
(1) combining a cyclosiloxane compound comprising $\leq 5$ ppm water, with hexafluoroacetone (HFA), to form a sample mixture comprising at least the cyclosiloxane compound and a water derivative of hexafluoroacetone; and
(2) measuring the concentration of the water derivative of hexafluoroacetone by gas chromatography.

In a still further aspect, the present invention relates to a method for production of a super dry cyclosiloxane precursor material comprising:
(1) a purification step selected from the group consisting of:
  (a) contacting a cyclosiloxane raw precursor material comprising at least trace water impurity, with an adsorbent bed material, so as to remove therefrom at least a portion of the water impurity chemically and physically, thereby producing a purified cyclosiloxane precursor material having a reduced level of water, and removing the purified cyclosiloxane precursor material from the adsorbent bed material;
  (b) distilling a raw material cyclosiloxane starting mixture comprising at least water and at least one cyclosiloxane precursor material, in the presence of an azeotropic component, so as to form an azeotropic mixture with the water contained in said starting mixture; in order to produce (A) a distillate fraction comprising water and the azeotropic component and (B) a balance fraction comprising a purified cyclosiloxane precursor material, whereby said balance fraction (B) is substantially reduced in water relative to the starting mixture;
  (c) distilling a raw material cyclosiloxane starting mixture comprising at least water and at least one cyclosiloxane precursor material, in the presence of hexafluoroacetone, so as to form a water derivative of hexafluoroacetone with the water contained in said starting mixture; in order to produce at least (A) a distillate fraction comprising the water derivative of hexafluoroacetone and (B) a second distillate fraction comprising a purified cyclosiloxane precursor material, whereby said second fraction (B) is substantially reduced in water relative to the starting mixture; and
  (d) any combination of the foregoing (a), (b) and (c); and
(2) combining the purified cyclosiloxane precursor material with at least a stoichiometric amount of hexafluoroacetone (HFA), to form a sample mixture comprising at least the cyclosiloxane precursor material and a water derivative of hexafluoroacetone; and
(3) measuring the concentration of the water derivative of hexafluoroacetone by gas chromatography.

Other aspects, features and embodiments of the invention will be more fully apparent from the ensuing disclosure and appended claims.

DETAILED DESCRIPTION OF THE INVENTION AND PREFERRED EMBODIMENTS THEREOF

U.S. patent application Ser. No. 10/015,326 entitled "Method for Removal of Impurities in Cyclic Siloxanes Useful as Precursors for Low Dielectric Constant Thin Films", filed in the United States Patent and Trademark Office on Dec. 13, 2001, and issued Sep. 19, 2006 as U.S. Pat. No. 7,108,771, is incorporated herein by reference in its entirety.

Although described hereinafter primarily in reference to cyclosiloxanes, it will be appreciated that the method of the invention is not thus limited, but rather is broadly applicable to the analysis of other materials and mixtures, as well as to other chemical reagents where trace water analysis is necessary. The present invention is applicable to the manufacturing and use of materials including liquids solids and gases, from all disciplines of technology, where trace water analysis is required and/or necessary, including but not limited to chemicals for semiconductor manufacturing, ion implantation, manufacture of flat panel displays, medical treatment, water treatment, emergency breathing equipment, welding operations, space-based applications involving delivery of liquids and gases, pharmaceutical applications, foodstuff industry, lubricating oil industry, etc.

The present invention is not limited, but rather is broadly applicable to the analysis of chemical reagents, siloxane materials and mixtures of the foregoing, where trace water analysis is required, as well as to chemical reagents where trace water analysis is not measurable by Karl Fischer titration and other methods. The ensuing discussion relating to cyclosiloxanes should therefore be understood to encompass all such other materials as disclosed hereinabove.

The present invention further relates to the accurate and precise measurement of water concentration in chemical reagents. More specifically, the present invention relates to the measurement of trace water concentration in chemical reagents by measuring a water derivative of an organic compound by gas chromatography.

In one embodiment, the invention relates to a process for measuring water concentration in chemical reagents to levels<40 ppm.

In one embodiment, the present invention relates to a process for the measurement of trace water concentration in chemical reagents comprising same, such process comprising the steps of:

(1) combining a chemical reagent comprising trace water, with hexafluoroacetone (HFA), to form a sample mixture comprising at least the chemical reagent and a water derivative of hexafluoroacetone; and (2) measuring the concentration of the water derivative of hexafluoroacetone by gas chromatography.

In a further embodiment, the present invention provides a process for measuring the concentration of water in cyclosiloxane materials, suitable for semiconductor device manufacturing applications, in which the cyclosiloxane material is useful as a precursor for producing porous, low-dielectric constant, SiO and SiCOH thin films of correspondingly high purity. Preferably, the process of the instant invention is useful for measuring water concentration in cyclosiloxane compounds to levels<30 ppm, more preferably <10 ppm and most preferably <5 ppm.

In a further embodiment the present invention relates to a process for the measurement of trace water concentration in cyclosiloxane compounds comprising:

(1) combining a cyclosiloxane compound comprising trace water, with hexafluoroacetone (HFA), to form a sample mixture comprising at least the cyclosiloxane compound and a water derivative of hexafluoroacetone; and (2) measuring the concentration of the water derivative of hexafluoroacetone by gas chromatography.

As used herein, the term "trace water concentration" is defined as having ≦40 ppm of water.

Hexafluoroacetone (HFA) is a gas at room temperature and may be bubbled directly into a sample, or the HFA may be injected into a sample by means of a gas tight syringe. The amount of hexafluoroacetone used should be in stoichiometric excess of the approximate concentration of water in the chemical reagent and such amount is readily determined by one skilled in the art. The hexafluoroacetone will react stoichiometrically with water (1:1), while excess hexafluoroacetone, which eludes separately and distinctly from the water derivative of the hexafluoroacetone, ensures that all water molecules in the sample to be measured are converted to the water derivative of the HFA.

In a preferred embodiment, HFA is injected by means of a gas tight syringe into a sample comprising at least a cyclosiloxane compound and trace water. The amount of hexafluoroacetone used is in stoichiometric excess of the approximate concentration of water in the chemical reagent.

Figure 1:
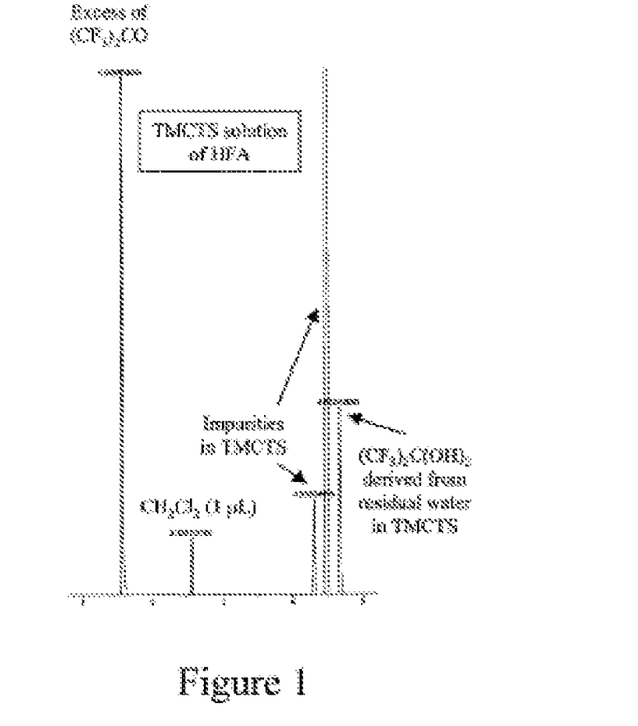
FIG. 1 shows a gas chromatograph analysis of a TMCTS sample showing residual water by organic derivatization according to one aspect of the present invention.

FIG. 1, shows a gas chromatograph according to one embodiment of the present invention. Excess hexafluoroacetone has been added to a sample of TMCTS comprising about 32 ppm trace water. As described hereinabove, the excess hexafluoroacetone ensures complete reaction and conversion of the trace water to the water derivative of hexafluoroacetone.

In the CVD process, a precursor is delivered to a CVD reactor in vapor form. In the case of solids and liquids, this requires heating of the delivery lines, CVD chamber and substrate. It is speculated that cyclosiloxanes, particularly TMCTS, prematurely polymerize in the heated delivery lines due to the presence of trace water in the raw cyclosiloxane material, through a ring opening mechanism. Trace acids and/or bases, which may be present in the CVD process, further accelerate the ring opening mechanism.

In current CVD processes, $CO_2$ and ammonia ($NH_3$) are used as reactant gases when depositing low dielectric thin films from cyclosiloxanes, particularly TMCTS. If the TMCTS is wet, $CO_2$ becomes $H_2CO_3$, which is a fairly strong acid, and ammonia becomes $NH_4OH$, which is a fairly strong base. As acids and bases promote TMCTS polymerization in the delivery tubes of the CVD apparatus, leading to delivery line plugging problems, it is necessary to use dry TMCTS. Accordingly, the instant invention provides a much-needed process for accurately measuring the water concentration in cyclosiloxane materials. (See applicants' currently pending application Ser. No. 10/015,326 entitled "Method for Removal of Impurities in Cyclic Siloxanes Useful as Precursors for Low Dielectric Constant Thin Films")

Figure 2:
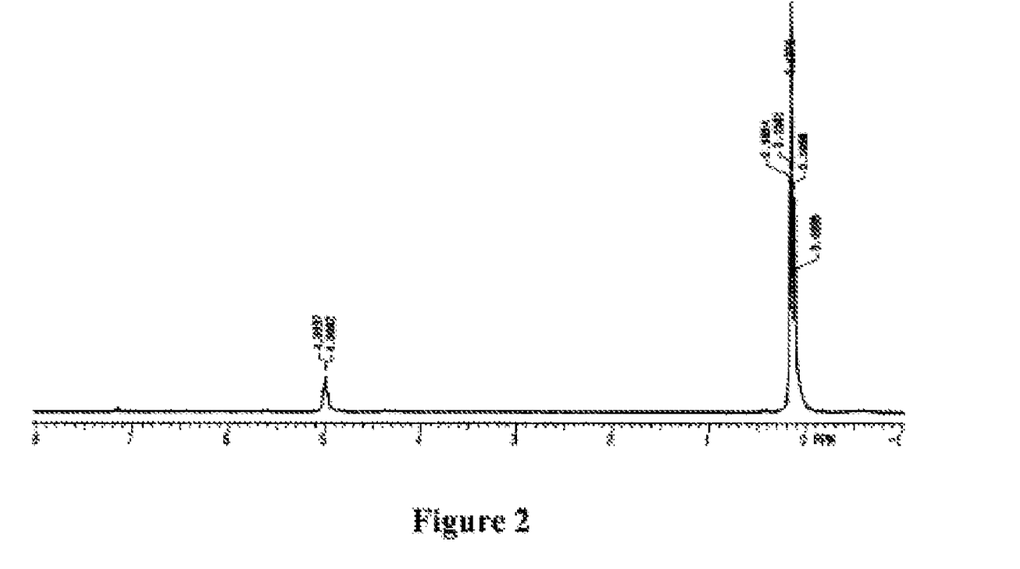
FIG. 2 shows a $^1$H NMR spectrum of raw TMCTS having 125 ppm of water.
Figure 3:
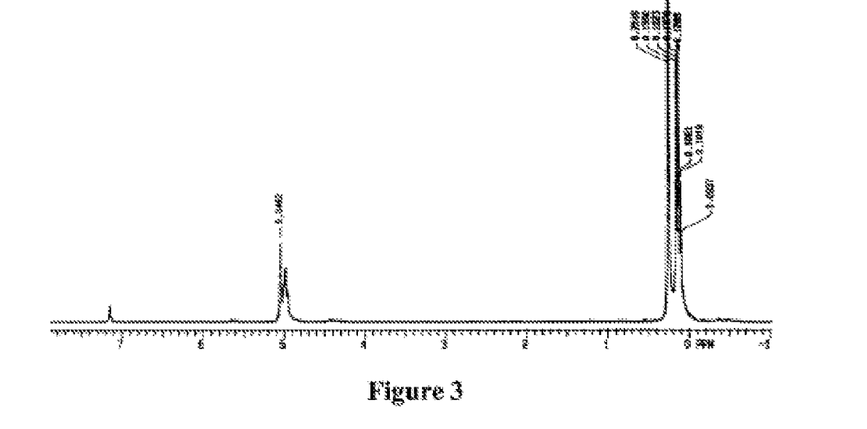
FIG. 3 shows a $^1$H NMR spectrum of Raw TMCTS having 125 ppm of water, after heating at 140° C. for 20 hours, showing a substantial amount of polymerized TMCTS.
Figure 4:
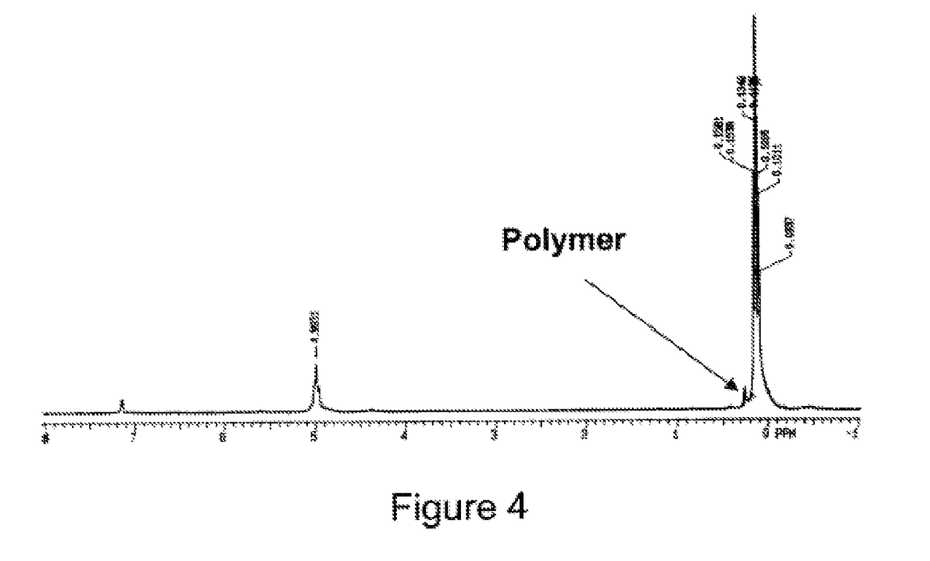
FIG. 4 shows a $^1$H NMR spectrum of super-dry TMCTS having 10 ppm of water, after heating at 140° C. for 20 hour, showing only 3-5% of polymerization.
Figure 5:
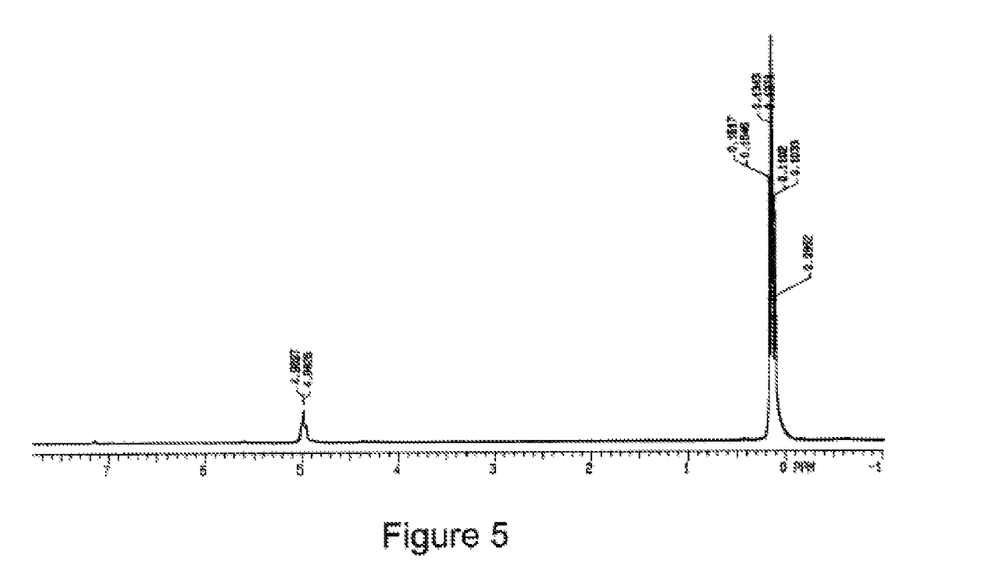
FIG. 5 shows a $^1$H NMR spectrum of super-dry TMCTS having 10 ppm of water, after drying over $CaH_2$, and distillation.

To determine whether water played a significant role in the polymerization of the TMCTS, the inventors of the instant invention developed a control experiment using $^1$H NMR to study such affects. FIG. 2, shows a $^1$H NMR spectrum of a commercial sample of raw TMCTS in $C_6D_6$ having a water content of approximately 125 ppm. The resonance of Si—H proton and $CH_3$ protons are shown at 4.98 and 0.165 ppm respectively. FIG. 3, shows by $^1$H NMR spectroscopy, the effect of heating the same sample as in FIG. 1, to 140° C. for 20 hours. The sample became visually viscous and partially polymerized as shown by $^1$H shifts in the Si—H peak from 4.98 to 5.04 and the $CH_3$ peak from 0.165 to 0.255. FIG. 3 shows significant polymerization of the TMCTS with 125 ppm water. The sample used in FIG. 3 was distilled at 140° C. for 20 hours. As shown by FIG. 4, a very small peak (less than 5%) at the position of the polymer resonances indicates formation of the polymer. Thus indicating the need for a highly efficient method for removing water from cyclosiloxane materials as well as the need for an analytical technique for measuring trace water concentrations. FIG. 5, shows a $^1$H NMR spectrum of a TMCTS sample after drying over $CaH_2$, followed by distillation according to one embodiment of the present invention. The sample having approximately 10 ppm of water shows no signs of polymerization.

U.S. patent application Ser. No. 10/015,326 entitled "Method for Removal of Impurities in Cyclic Siloxanes Useful as Precursors for Low Dielectric Constant Thin Films", filed on Dec. 13, 2001, and incorporated herein by reference in its entirety, discloses a novel method of purifying siloxanes, particularly cyclosiloxanes having impurity levels from 1 to 20 ppm. As cyclosiloxanes are foreseen by the semiconductor industry as viable candidates for the development and implementation of new low-dielectric constant materials, it is imperative that methods are available to purify and characterize such materials.

Gas chromatography (GC) is a standard technique used in many laboratories and industrial facilities and is useful in analyzing mixtures of volatile substances. Gas chromatographs may be used alone, with various detectors such as flame ionization detector, thermionic emission detector, photo ionization detector, electron capture detector (ECD) and others, or with a mass spectrometer as a detector. In such applications, a gas chromatography (GC) column separates sample components from a sample mixture. In such an application, the gas chromatography (GC) column separates the sample components from the sample mixture and the mass spectrometer analyzes and quantifies the sample components.

By converting water to a volatile organic compound through derivatization, the inventors of the instant invention have developed an accurate and precise means by which to measure water in cyclosiloxane materials to levels as low as $\leq 1$ ppm.

In a further embodiment, the present invention relates to an analytical technique for the accurate and precise measurement of trace water in cyclosiloxane materials comprising:

(1) combining a cyclosiloxane compound comprising $\leq 40$ ppm water, with hexafluoroacetone (HFA), to form a sample mixture comprising at least the cyclosiloxane compound and a water derivative of hexafluoroacetone; and (2) measuring the concentration of the water derivative of hexafluoroacetone by gas chromatography.

In one embodiment, the cyclosiloxane material comprises the formula [R R'Si—O]$_n$ wherein each of R and R' is same or different and independently selected from the group consisting of hydrogen, $C_1$-$C_8$ alkyl, $C_1$-$C_8$ alkoxy, $C_1$-$C_8$ alkene, $C_1$-$C_8$ alkyne, and $C_1$-$C_8$ carboxyl; and n is from 2 to 8. In a preferred embodiment, the cyclosiloxane is selected from the group consisting of: polyhedral oligomeric silsesquioxanes (POSS), octamethylcyclotetrasiloxane (OMCTS), more specifically 1,1,3,3,5,5,7,7-octamethylcyclotetrasiloxane (OMCTS), hexamethylcyclotetra-siloxane (HMCTS), more specifically 1,1,3,5,5,7-hexamethylcyclotetrasiloxane (HMCTS), tetramethylcyclotetrasiloxane (TMCTS), more specifically 1,3,5,7-tetramethylcyclotetrasiloxane (TMCTS), and mixtures thereof. In the most preferred embodiment, the cyclosiloxane material is 1,3,5,7-tetramethylcyclotetrasiloxane (TMCTS).

The organic molecule selected for derivatization should have certain characteristics, including but not limited to:
  must elude off the gas chromatography column;
  must react stoichiometrically with the water molecule;
  must be inert with the siloxane;
  must be volatile and accurately measurable by gas chromatography;
  The water derivative of the organic molecule formed, must be volatile and accurately measurable by gas chromatography, must elude from the column at a different time from the organic molecule and must be inert with the siloxane material.

In one embodiment, the organic molecule is selected from the group consisting of: hexafluoracetylacetone (Hhfac), fluorocarboxylic acids, and hexafluoroacetone. Preferably, the organic molecule is hexafluoracetone.

In a further embodiment, the present invention relates to a process for the measurement of trace water concentration in tetramethylcyclotetrasiloxane (TMCTS), wherein said process comprises the steps of:

(1) combining tetramethylcyclotetrasiloxane comprising trace water, with hexafluoroacetone (HFA) to form a sample mixture comprising at least tetramethylcyclotetrasiloxane and a water derivative of hexafluoroacetone; and (2) measuring the concentration of the water derivative of hexafluoroacetone $((CF_3)_2C(OH)_2)$ by gas chromatography.

Hexafluoroacetone reacts rapidly and quantitatively with water at room temperature, according to the following equation:

$$(CF_3)_2CO + H_2O \rightarrow (CF_3)_2C(OH)_2 \qquad (3)$$

The conditions for the various parameters for the gas chromatograph and other related ancillaries as used in the instant invention, with regard to such parameter as, column specifications, column temperature, sample size, detector temperature, injector temperature, internal standard, carrier gas flow, and carrier gas type, are readily determined by skilled artisans in analytical chemistry. In one embodiment, the conditions for gas chromatograph with a mass spectrometer include but are not limited to:
  column type: amine such as an RTX-5 available commercially from RESTEK;
  oven temperature program: 35° C. (2 minutes)/ramped to 100° C. at 10° C./min/held at 100° C. for 2 minutes;
  detector temperature: 100° C.; and
  injector temperature: 100° C.
  internal standard $CH_2Cl_2$.

In one embodiment, the injector temperature of the gas chromatograph is set to ≦100° C. to prevent decomposition of the water derivative of the hexafluoroacetone back to water and HFA.

The derivatization and measurement steps of the instant invention, may be carried out at any time during the purification process of a cyclosiloxane material. However, most preferably, the derivatization and trace water measurement steps are carried out after the cyclosiloxane material has been purified at least once. Methods useful in purifying cyclosiloxane compounds to levels acceptable by the semiconductor industry include the methods outlined in applicants' pending U.S. patent application Ser. No. 10/015,326 entitled "Method for Removal of Impurities in Cyclic Siloxanes Useful as Precursors for Low Dielectric Constant Thin Films", filed on Dec. 13, 2001, and incorporated herein by reference in its entirety. Purification methods include but are not limited to, distillation, azeotropic distillation, use of absorbent materials which remove water either physically or chemically via adsorption or reaction; filtration, extraction and, combinations of the foregoing.

In a still further aspect, the present invention relates to a method for production of a super dry cyclosiloxane precursor material comprising:

(1) a purification step selected from the group consisting of:
   (a) contacting a cyclosiloxane raw material comprising at least trace water impurity, with an adsorbent bed material/drying agent, so as to remove therefrom at least a portion of the water impurity, thereby producing a purified cyclosiloxane material having a reduced level of water, and removing the purified cyclosiloxane material from the adsorbent bed material;
   (b) distilling a raw material cyclosiloxane starting mixture comprising at least water and at least one cyclosiloxane, in the presence of an azeotropic component, so as to form an azeotropic mixture with the water contained in said starting mixture; in order to produce (A) a distillate fraction comprising water and the azeotropic component and (B) a balance fraction comprising a purified cyclosiloxane material, whereby said balance fraction (B) is substantially reduced in water relative to the starting mixture; and
   (c) distilling a raw material cyclosiloxane starting mixture comprising at least water and at least one cyclosiloxane precursor material, in the presence of hexafluoroacetone, so as to form a water derivative of hexafluoroacetone with the water contained in said starting mixture; in order to produce at least (A) a distillate fraction comprising the water derivative of hexafluoroacetone and (B) a second distillate fraction comprising a purified cyclosiloxane precursor material, whereby said second fraction (B) is substantially reduced in water relative to the starting mixture; and
   (d) any combination of the foregoing (a), (b) and (c); and
(2) combining the purified cyclosiloxane material with at least a stoichiometric amount of hexafluoroacetone (HFA), to form a sample mixture comprising at least the cyclosiloxane compound and a water derivative of hexafluoroacetone; and
(3) measuring the concentration of the water derivative of hexafluoroacetone by gas chromatography.

As used herein an adsorbent and or drying agent is defined as a substance that absorbs water and or other impurities. Drying agents and/or adsorbents are grouped into two major classes: chemically acting and physically acting drying agents.

Chemically acting drying agents are substances that bind water in the form of crystallization and may be regenerated by warming. Examples of these types of drying agents are calcium chloride, sodium sulfate, or magnesium sulfate. The second subdivision of chemically acting drying agents is substances that react with water. Regeneration of these drying agents is not possible since the drying agent has undergone a chemical change. Examples of these types of drying agents are, phosphorus pentoxide, metals, and metal hydrides, such as calcium hydride and HFA.

Physically acting drying agents are substances that adsorb water and or other impurities on the surface and in the pores of the drying agent. These drying agents can be regenerated by warming or applying a vacuum. Examples of these types of drying agents are desiccant, silica gel, molecular sieves, activated carbon and aluminum oxide.

The adsorbent bed material used in the purification process of the instant invention may comprise one of many adsorbents and/or drying agents and/or mixtures thereof, having affinity for water and/or at least one acidic impurity. Such adsorbents are readily known to those skilled in the art. For example, the adsorbent may comprise activated carbon adsorbent, (beads or powder), having an average particle size of from about 30 to 50 μm with a pore size distribution of from about 10 to 50 nm. The drying agent may comprise a liquid or a gaseous material, such as HFA. Further, the adsorbent bed material may comprise molecular sieves, having a particle size distribution from about 100 to 125 μm and a pore size distribution from about 10 to 50 nm. Still further, the adsorbent bed material may comprise calcium hydride, or calcium oxide, etc. In a preferred embodiment, the adsorbent is selected from calcium oxide and calcium hydride.

In one embodiment, the adsorbent bed material may comprise a combination or series of adsorbents and/or drying agents. For example, the cyclosiloxane precursor may first contact a drying agent such as calcium hydride to adsorb water molecules and separately contact a carbon adsorbent material for adsorption of an acidic impurity. As a second example the adsorbent bed material may comprise a combination of both calcium hydride and carbon adsorbent to remove both water and acidic impurity in a single step.

The amount of adsorbent used is dependent on the concentration of water and optionally other impurities present in the cyclosiloxane precursor material to be purified and the capacity of the adsorbent bed material. In one embodiment, the adsorbent may be useful in reducing water levels to <20 ppm.

The adsorbent bed material may be placed in a distillation flask or in a separate column so long as the cyclosiloxane to be purified contacts the adsorbent bed material for a period of time sufficient to remove at least a portion of the impurity from the cyclosiloxane precursor. In one embodiment, the cyclosiloxane precursor contacts the adsorbent bed material from about 1 minute to about 10 hours, more preferably from about 30 minutes to 2 hours.

As used herein, the term "azeotrope" is defined as a constant boiling mixture, having a fixed composition, which cannot be altered by normal distillation. The azeotropic component employed in the invention should form an azeotrope with water. Azeotropic components useful in the purification step of the instant invention include but are not limited to benzene, ethanol, 2-propanol, butyl acetate, phenol, chloroform, methyl acrylate, isopropyl formate, isopropyl acetate, cyclohexane, di-iso-propyl ether, toluene and n-heptane. A particularly preferred azeotropic component useful in the present invention is benzene, which forms an azeotrope with water at 69.4° C.

Figure 6:
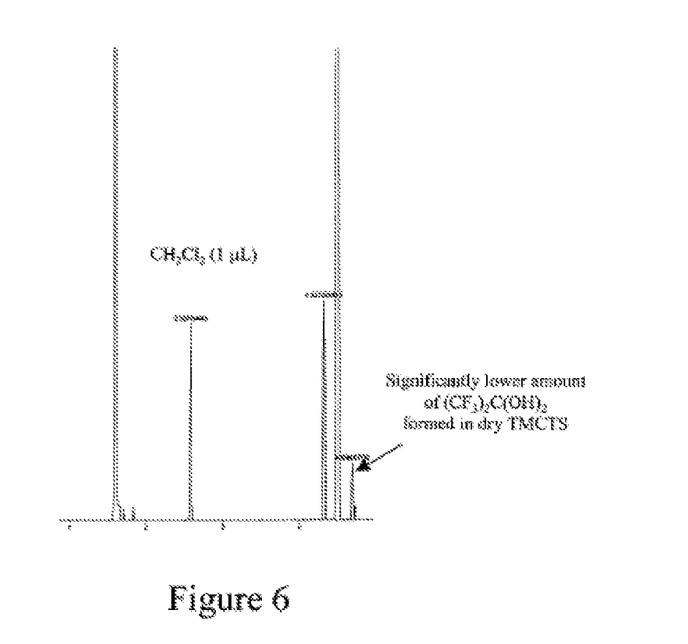
FIG. 6 shows a gas chromatograph analysis of super dry TMCTS having a water concentration of approximately 3 ppm, according to a further aspect of the present invention.

FIG. 6 shows a gas chromatograph analysis of super dry TMCTS according to a further embodiment of the present invention. A batch of commercially available TMCTS having an original water concentration of about 125 ppm is refluxed over $CaH_2$ for 12 hours and subsequently distilled. The water concentration in the distilled TMCTS was about 3 ppm as shown and identified in FIG. 6.

In a further embodiment the present invention relates to a real-time gas-chromatography mass-spectrometry method of analyzing trace water in cyclosiloxane precursors. A sampling valve distributes an aliquot of cyclosiloxane from a reaction vessel or other containment system and introduces the cyclosiloxane aliquot into a mixing chamber, where HFA and a GC standard are combined and mixed aliquot, to form a sample for GC analysis. The sample contains at least the cyclosiloxane, unreacted HFA, water derivatized HFA and standard. An aliquot of the sample is transferred by carrier gas to a micro-accumulator, where it is delivered to the gas chromatography column, for separation of the sample into sample components and transport of the sample components to a mass spectrometer for trace water detection and analysis or testing in real time.

The features, aspects and advantages of the present invention are further shown with reference to the following non-limiting example relating to the invention.

EXAMPLES

Example 1

Gas Chromatography Mass Spectrometer, Method Validation

Three analytical samples, including an analytical standard, all containing water, were measured using the water derivative of hexafluoroacetone method (HFA). For purposes of method validation, the same samples were also measured using the Karl Fischer titration method of water analysis. As shown by the results in Table 1 below, the HFA method produced water measurements relatively similar to the Karl Fischer water titration method. With respect to the analytical standard for water, the HFA method measured the water content with a higher accuracy, than did the Karl Fischer water analysis method.

TABLE 1

Comparison of Water analysis Results (in ppm)

|  | HFA Method | Karl Fischer |
|---|---|---|
| Anhydrous toluene | 9.5 | 11.5 |
| $H_2O$ saturated toluene | 276 | 311 |
| Analytical standard (100 ppm) | 95 | 91 |

Example 2

Gas Chromatography Mass Spectrometer Precision Validation

To determine the precision of the HFA method of water analysis, an analytical standard of 100 ppm water is measured five times. Table 2 shows the results of the water concentration measurement as well as the mean and the mean error.

TABLE 2

Analytical Standard Measurement of 100 ppm Water Sample by HFA Method

| Run Number | Water (ppm) | R(%) |
|---|---|---|
| 1 | 99.67 | 4.942 |
| 2 | 92.94 | 2.144 |
| 3 | 85.10 | 10.398 |
| 4 | 89.69 | 5.566 |
| 5 | 107.48 | 13.165 |
| Mean | 94.98 | |

Example 3

Statistical Validation of HFA Method

To confirm the precision of the HFA method of water analysis, two samples from a single batch of purified tetramethylcyclotetrasiloxane (TMCTS) were measured five times each using the water derivative of hexafluoroacetone method of the instant invention. Table 3 shows the results of the water concentration measurement as well as the mean and the mean error for both samples.

TABLE 3

HFA Water Analysis of Dried TMCTS

| Run Number | Water (ppm) | R(%) | Run Number | Water (ppm) | R(%) |
|---|---|---|---|---|---|
| 1 | 10.62 | 15.023 | 1 | 12.03 | 2.278 |
| 2 | 11.24 | 10.062 | 2 | 12.01 | 2.108 |
| 3 | 13.89 | 11.142 | 3 | 12.17 | 3.469 |
| 4 | 14.24 | 13.943 | 4 | 10.61 | 9.794 |
| 5 | Nd | Nd | 5 | 11.99 | 1.938 |
| Mean | 12.497 | | Mean | 11.762 | |

Example 4

Gas Chromatograph Showing Sensitivity Experiment of HFA Water Analysis Method

Figure 7A:
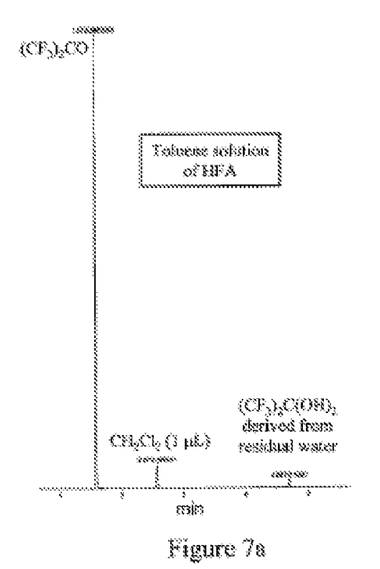
FIGS. 7a and 7b show a sensitivity ratio of water-derivatized hexafluoroacetone $((CF_3)_2C(OH)_2)$ to methylene chloride $(CH_2Cl_2)$ by gas chromatography.
Figure 7B:
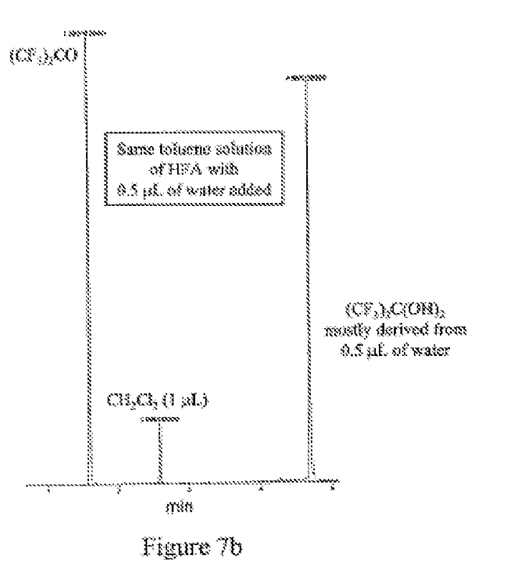

FIG. 7a shows the formation $(CF_3)_2C(OH)_2$ derived from the residual water of anhydrous toluene relative to methylene chloride $(CH_2Cl_2)$ used as internal reference. The relative sensitivity ratio of water-derivatized hexafluoroacetone diol $(CF_3)_2C(OH)_2$ (formed from the excess of HFA and 0.5 µL of water) to 1 µL of methylene chloride $(CH_2Cl_2)$ can be calculated based on the peak integration intensities, see FIG. 7b.

What is claimed is:

1. A cyclosiloxane composition comprising a cyclosiloxane and a water derivative of hexafluoroacetone.

2. The cyclosiloxane composition of claim 1, wherein the cyclosiloxane has the formula $[RR'Si—O]_n$, wherein each of R and R' is same or different and independently selected from the group consisting of hydrogen, $C_1$-$C_8$ alkyl, $C_1$-$C_8$ alkoxy, $C_1$-$C_8$ alkene, $C_1$-$C_8$ alkyne, and C $C_1$-$C_8$ carboxyl and n is from 2 to 8.

3. The cyclosiloxane composition of claim 1, wherein the cyclosiloxane material is 1,3,5,7-tetramethylcyclotetrasiloxane (TMCTS).

4. The cyclosiloxane composition of claim 1, wherein the cyclosiloxane compound is selected from the group consisting of octamethylcyclotetrasiloxanes (OMCTS), hexamethylcyclotetra-siloxanes (HMCTS), tetramethylcyclotetrasi-loxanes (TMCTS), and mixtures thereof.

5. The cyclosiloxane composition of claim 1, having a trace water concentration of ≦40 ppm when measured by a process comprising (1) combining the cyclosiloxane composition with at least a stoichiometric amount of gaseous hexafluoroacetone (HFA), to form a corresponding sample composition in which trace water has been converted to a water derivative of hexafluoroacetone, and (2) measuring the concentration of the water derivative of hexafluoroacetone in said sample composition by gas chromatography.

6. The cyclosiloxane composition of claim 5, having a trace water concentration of ≦30 ppm when measured by said process.

7. The cyclosiloxane composition of claim 5, having a trace water concentration of ≦20 ppm when measured by said process.

8. The cyclosiloxane composition of claim 5, having a trace water concentration of ≦10 ppm when measured by said process.

9. The cyclosiloxane composition of claim 5, having a trace water concentration of ≦5 ppm when measured by said process.

10. The cyclosiloxane composition of claim 5, having a trace water concentration of ≦5 ppm when measured by said process.

11. The cyclosiloxane composition of claim 5, having a trace water concentration of ≦1 ppm when measured by said process.

12. The cyclosiloxane composition of claim 5, having a trace water concentration of 1 to 20 ppm when measured by said process.

13. The cyclosiloxane composition of claim 1, wherein the water derivative of hexafluoroacetone is $(CF_3)_2C(OH)_2$.

14. The cyclosiloxane composition of claim 1, wherein the amount of hexafluoroacetone combined with the cyclosiloxane composition is in stoichiometric excess of the trace water concentration in said cyclosiloxane composition.

15. The cyclosiloxane composition of claim 1, wherein the gas chromatography includes use of a gas chromatograph that further comprises a mass spectrometer.

16. The cyclosiloxane composition of claim 1, wherein the sample composition further comprises an internal standard.

17. The cyclosiloxane composition of claim 1, wherein the internal standard is $CH_2Cl_2$.

18. The cyclosiloxane composition of claim 1, wherein the gas chromatography includes use of a gas chromatograph that comprises an injector that is set at a temperature of ≦100° C.

19. A composition comprising compound selected from the group consisting of polyhedral oligomeric silsesquioxanes (POSS), octamethylcyclotetrasiloxanes (OMCTS), hexametbylcyclotetra-siloxanes (HMCTS), tetramethylcyclotetrasiloxanes (TMCTS), and mixtures thereof, and a water derivative of hexafluoroacetone.

20. The cyclosiloxane composition of claim 19, having a trace water concentration of ≦40 ppm when measured by a process comprising (1) combining the cyclosiloxane composition with at least a stoichiometric amount of gaseous hexafluoroacetone (HFA), to form a corresponding sample composition in which trace water has been converted to a water derivative of hexafluoroacetone, and (2) measuring the concentration of the water derivative of hexafluoroacetone in said sample composition by gas chromatography.

* * * * *